United States Patent [19]

Ito et al.

[11] Patent Number: 5,071,863

[45] Date of Patent: Dec. 10, 1991

[54] 4,5,6,7-TRISUBSTITUTED BENZOXAZOLONES

[75] Inventors: Fumitaka Ito, Chita; Takashi Mano, Handa; Masami Nakane, Nagoya, all of Japan

[73] Assignee: Pfizer Inc., New York, N.Y.

[21] Appl. No.: 554,625

[22] Filed: Jul. 18, 1990

[30] Foreign Application Priority Data

Jul. 20, 1989 [JP] Japan ............................. 63-188683

[51] Int. Cl.$^5$ .................... C07D 263/58; A61K 31/42
[52] U.S. Cl. .................................. 514/338; 514/375; 546/270; 548/221
[58] Field of Search ................ 514/375, 338; 548/221; 546/270

[56] References Cited

U.S. PATENT DOCUMENTS

| | | | |
|---|---|---|---|
| 3,256,293 | 6/1966 | Baker et al. | 548/221 |
| 3,657,265 | 4/1972 | Kober | 548/221 |
| 3,929,817 | 12/1975 | Draber | 548/221 |
| 4,227,915 | 10/1980 | D'Amico | 548/221 |
| 4,835,166 | 5/1989 | Kitaura et al. | 514/375 |
| 4,904,685 | 2/1990 | Kitaura et al. | 514/418 |
| 5,006,541 | 4/1991 | Kitaura | 546/270 |

FOREIGN PATENT DOCUMENTS

| | | | |
|---|---|---|---|
| 249407 | 12/1987 | European Pat. Off. | |
| 0123103 | 7/1982 | Japan | 548/221 |
| 0093283 | 4/1987 | Japan | 548/221 |
| 8501289 | 9/1983 | World Int. Prop. O. | 514/375 |

OTHER PUBLICATIONS

Clark et al., Jour. Am. Chem. Soc., vol. 80, pp. 1662–1664, (1958).

Primary Examiner—Donald G. Daus
Attorney, Agent, or Firm—Peter C. Richardson; J. Trevor Lumb; A. Dean Olson

[57] ABSTRACT

Certain 6-aryl- or 6-heteroaryl- alkylaminobenzoxazolones, and their pharmaceutically-acceptable salts, are dual inhibitors of lipoxygenase and cyclooxygenase enzymes, and so are useful as antiallergy and antiinflammatory agents.

10 Claims, No Drawings

4,5,6,7-TRISUBSTITUTED BENZOXAZOLONES

BACKGROUND OF THE INVENTION

The present invention relates to certain novel derivatives of 6-aryl-or 6-heteroaryl-alkylaminobenzoxazolone, and they are further variously substituted at the 4, 5 and 7-positions. These compounds are dual inhibitors of LO (lipoxygenase) and CO (cyclooxygenase) enzymes, and are useful as antiallergy and antiinflammatory agents in mammalian subjects.

European patent application (published Dec. 16, 1987 under No. 2449407) by Kitaura discloses related benzoxalone compounds having an aryl- or heteroarylalkylamino group at the 6-position, which are dual LO and CO inhibitors.

In PCT Patent Application WO 85/01289 there are described and claimed a number of benzoxazolone and benzothiazolone derivatives which are useful for the treatment of inflammatory conditions and thrombosis. There is no disclosure of any aryl alkyl-amino substituted benzoxalolones. Also, dual inhibition of the LO and CO is not reported for these prior art compounds.

SUMMARY OF THE INVENTION

The present invention provides novel benzoxazolone compounds of the formula:

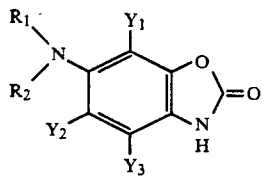

or a pharmaceutically acceptable acid addition salt thereof wherein $R_1$ is hydrogen or $C_1-C_3$ alkyl;
$R_2$ is a group of the formula —$(CH_2)_m$—Ar or —$(CH_2)_m$—Het wherein m is an integer of 1 to 6 and Ar is phenyl optionally substituted by one or more radicals selected from $(C_1-C_3)$ alkyl, $(C_1-C_3)$ alkoxy, $(C_1-C_3)$ alkylthio, halo, $(C_1-C_2)$ alkylamino or hydroxyl; Het is selected from furyl, thienyl, pyridyl, pyrrolyl, imidazolyl, pyranyl, oxazolyl or indazolyl; and $Y_1$, $Y_2$ and $Y_3$ are each independently hydrogen, $(C_1-C_3)$ alkyl, halo or $(C_1-C_3)$ alkoxy or trifluoromethyl; with the proviso that at least two of $Y_1$, $Y_2$ and $Y_3$ are other than hydrogen.

"Halo" means fluoro, chloro or bromo.

Preferred compounds are those wherein $R_1$ is hydrogen.

Within this preferred group of compounds, preferred values for $Y_1$, $Y_2$ and $Y_3$ are each independently hydrogen, $(C_1-C_3)$ alkyl or fluoro. Preferred values of m are 1, 2 and 3. Preferred Ar radicals are phenyl optionally substituted with methyl, most preferably unsubstituted phenyl. Preferred "Het" are pyridyl, and pyranyl.

The most preferred compounds have m as 1 and either $Y_1$ or $Y_3$ as hydrogen. Within this group, when $Y_1$ is hydrogen $Y_2$ and $Y_3$ are each preferably methyl or fluoro. When $Y_3$ is hydrogen, $Y_1$ and $Y_2$ are then each preferably methyl or fluoro. Especially preferred individual compounds of this invention are:
6-[(Tetrahydropyran-3-yl)methylamino]-4-fluoro-5-methyl-2-benzoxazolone;
6-Benzylamino-4-fluoro-5-methyl-2-benzoxazolone; and
6-Benzylamino-5-fluoro-4-methyl-2-benzoxazolone.

Additionally, the favored and preferred intermediates of formulae (III) and (IV) may serve as intermediates for the favored and preferred compounds of formula (I).

The pharmaceutically acceptable acid addition salts of the compounds of the formula (I) are those formed from acids which form non-toxic acid addition salts, for example, the hydrochloride, hydrobromide, sulfate or bisulfate, phosphate or acid phosphate, acetate, citrate, fumarate, gluconate, lactate, maleate, succinate, tartrate, methanesulfonate, benzene sulfonate and toluenesulfonate, formate salts.

The present invention includes a pharmaceutical composition comprising a pharmaceutically acceptable carrier or diluent and a compound of formula (I), and a method for treating an allergic or inflammatory condition in a mammal, especially man, which comprises administering to said mammal an antiallergy or antiinflammatory effective amount of a compound of formula (I).

Also embraced by the present invention is a method of inhibiting the action of the lipoxygenese as well as the action of the cyclooxygenase in a mammal, which comprises administering to such mammal a lipoxygenase and cyclooxygenase inhibiting amount of a compound of formula (I).

DETAILED DESCRIPTION OF THE INVENTION

The novel compounds of formula (I) may be prepared as shown below in scheme 1. The intermediate compounds of formulae, (IV) and (V) in the scheme are novel compounds.

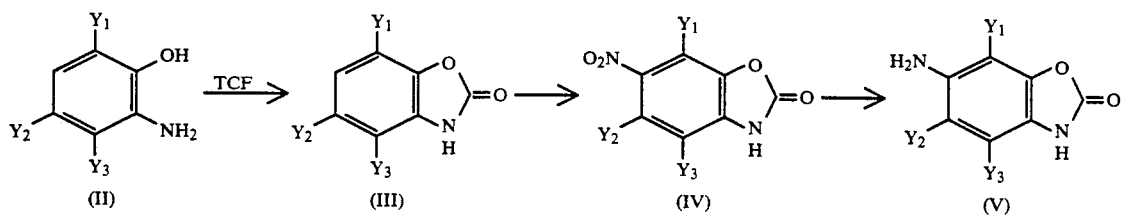

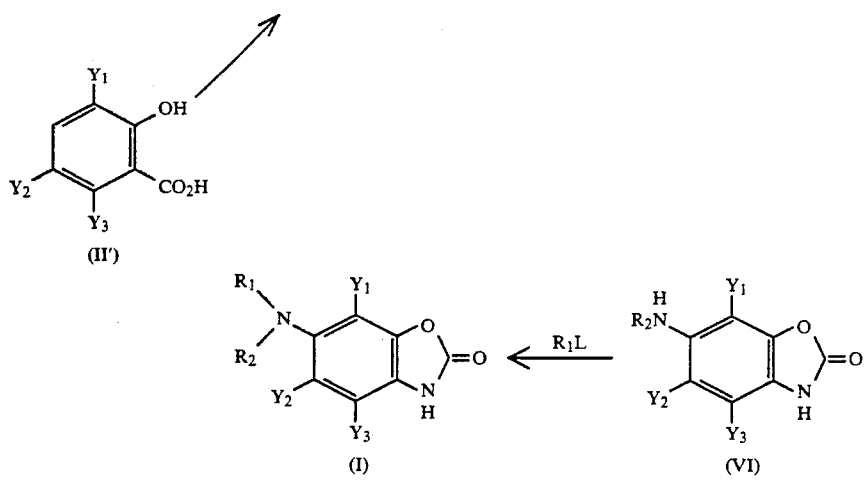

In the above formulae, m, $R_1$, $R_2$, $Y_1$, $Y_2$, $Y_3$ and are as previously defined. L is a facile leaving group such as cl, Br, I.

In the first step an aminophenol of formula (II) containing the desired substituents $Y_1$, $Y_2$ and $Y_3$ is cyclized to the corresponding benzoxazolone (III). The cyclization is performed by reacting the compound (II) with trichloromethyl chloroformate (TCF). As will be apparent to one skilled in the art, TCF can be replaced by urea. Suitable solvents for this reaction include ethyl acetate, tetrahydrofuran, dioxane, dimethoxyethane, and toluene. When urea is employed, the reaction does not necessarily require a solvent. The cyclization may be carried out over a wide range of temperatures. However, a temperature of from about 0° C. up to the reflux temperature of the solvent is preferred, at which temperature the reaction is complete in 1 to 24 hours. A base may be needed to facilitate this cyclization. The preferred bases are triethylamine, sodium ethoxide, sodium hydride, sodium carbonate and potassium carbonate. The resultant solid product is isolated by conventional methods and purified, if desired.

A salicilate of formula (II') containing desired substituents $Y_1$, $Y_2$, and $Y_3$ is also effectively converted to the corresponding benzooxazolone (III) using diphenylphosphoryl azide. Suitable solvents for this reaction include toluene, xylene, benzene and tetrahydrofurane. This reaction generally requires the reflux temperature of the solvent. The products can be isolated by a conventional manner.

Nitration of benzoxazolone (III) followed by hydrogenation provides compound (V). The nitration is typically carried out by stirring (III) in concentrated nitric acid at a temperature of from 0° C. to 90° C. Solvents such as acetic acid, acetic anhydride and nitromethane can also be used together with nitric acid. Upon completion of the reaction, the product is recovered in standard manners. Nitrobenzoxazolone (IV) is then converted to aminobenzoxazolone (V) by hydrogenation. This hydrogenation is accomplished in the presence of a noble metal catalyst such as palladium (Pd/c) with low hydrogen pressures (1 to 3 atm). Temperature is not critical but preferably ambient temperature. The solvent for hydrogenation should be, for example, methonal or ethanol. Hydrogenation proceeds to completion in about one hour to overnight. The product is again recovered conventionally, e.g. filtration, isolation and recrystallization.

The next step (V) to (VI) involves an imine formation followed by reduction of the intermediate imine. Thus, compound (V) is condensed with an aldehyde of formula Ar—$(CH_2)_{m-1}$—CHO or Het—$(CH_2)_{m-1}$—CHO where "Ar", "Het" and m are as defined previously. the reagents are contacted in equimolar amounts in the presence of a suitable solvent. A preferred solvent for both reactions is ethanol. Temperatures of from about room temperature up to the reflux temperature of the solvent can be employed in the first condensation. Typical reaction times are from 1 to 6 hours. A dehydrating agent can be used to accelerate the condensation, although it is not ordinarily required. Such dehydrating agents include molecular sieves, magnesium sulfate, potassium hydrogensulfite and sodium sulfate. The second reduction calls for a metal hydride, preferably sodium borohydride, sodium cyanoborohydride or lithium cyanoborohydride. The solvent for this reduction should be a protic alcoholic solvent, e.g., methanol, ethanol or isopropanol. Reaction temperature is not critical and preferably ambient temperature. The reaction is complete in 1 to 24 hours.

This reduction can also be effected by catalytic hydrogenation, which employs a catalytic amount of noble metals such as Pd, Pt, Ni, or Rh under atmospheric hydrogen. Common solvents for this reduction include methanol, ethanol, ethyl acetate, and tetrahydrofurane.

The product of formula (VI) can be isolated and purified by conventional procedures, such as recrystallization or chromatography.

Compounds of formula (I) wherein R is other than hydrogen are obtained by further reacting (VI) with $R_1L$. An alternate but favored procedure for preparing compounds (I wherein $R_1$ is methyl comprises condensation of (I) with formaldehyde and subsequent reduction of the in situ generated immonium salt. A preferred agent for reduction is sodium borohydride. Thus compound (I), formaldehyde and sodium borohydride are combined at a temperature between 0° to 25° C. in a solvent such as ethanol. The product can be isolated and purified conventionally.

The starting materials of formula (II) are either known compounds or easily prepared from commercially available materials by standard synthesis.

The pharmaceutically acceptable salts of the novel compounds (I) of the present invention are readily prepared by contacting said compound with a stoichiometric amount of an appropriate mineral or organic acid in either aqueous solution or in a suitable organic solvent. The salt may then be obtained by precipitation or by evaporation of the solvent.

The compounds of this invention possess inhibiting activity on the action of the cyclooxygenase as well as on the action of the lipoxygenase. This activity has been demonstrated by an assay using rat peritoneal cavity resident cells which determines the effect of said compounds on the metabolism of arachidonic acid.

In this test some preferred compounds indicate low IC50 values, in the range of 0.5 to 30 μM, with respect to both lipoxygenease/cyclooxygenase inhibitions.

The ability of the compounds of the present invention to inhibit both enzymes make them useful for controlling the symptoms induced by the endogenous metabolites arising from arachidonic acid in a mammalian subject. The compounds are therefore valuable in the prevention and treatment of such disease states in which the accumulation of said arachidonic acid metabolite is the causative factor, e.g., allergic bronchial asthma, skin disorders, rheumatoid arthritis, osteoarthritis, and thrombosis. The activity of the compounds of this invention can also be demonstrated in the standard carrageenin—induced rat foot edema test (C. A. Winter et al., Proc. Soc. Exp. Biol. III, p544, 1962).

Thus, compounds (I) and their pharmaceutically acceptable salts are of particular use in the treatment or alleviation of allergic or inflammatory conditions in a human subject.

For treatment of the various conditions described above, the compounds of formula (I) and their pharmaceutically acceptable salts can be administered to a human subject either alone, or, preferably, in combination with pharmaceutically-acceptable carriers or diluents in a pharmaceutical composition, according to standard pharmaceutical practice. A compound can be administered by a variety of conventional routes of administration including orally, parentally and by inhalation. When the compounds are administered orally, the dose range will be from about 0.1 to 20 mg/kg body weight of the subject to be treated per day, preferably from about 0.1 to 1.0 mg/kg per day in single or divided doses parenteral administration is desired, then an effective dose will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compound of formula (I) can be administered, for example, in the form of tablets, powders, lozenges, syrups or capsules, or as an aqueous solution or suspension. In the case of tablets for oral use, carriers which are commonly used include lactose and corn starch, and lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered intravenous use, the total concentration of solute should be controlled to make the preparation isotonic. The present invention is illustrated by the following examples. However, it should be understood that the invention is not limited to the specific details of these examples. Proton nuclear magnetic resonance spectra (NMR) were measured at 270 MHz unless otherwise indicated for solutions in perdeuterodimethyl sulfoxide (DMSO-d$_6$) and peak positions are expressed in parts per million (ppm) downfield from tetramethylsilane. The peak shapes are denoted as follows: s, singlet; d, doublet; t, triplet; m, multiplet; b, broad.

EXAMPLE 1

5-Fluoro-4-methyl-6-nitro-2-benzoxazolone

5-Fluoro-4-methyl-2-benzoxazolone (Preparation A, 2.01 g, 12 mmoles) was treated with concentrated nitric acid (24 ml) at room temperature under stirring. The mixture was heated to 50° C. and stirring continued for 20 minutes. Ice and water were added to the mixture and the resulting solids were collected, and washed with water and then with ethanol. The crude product was dried under reduced pressure and recrystallized from ethanol to give 1.84 g (72%) of the title compound: m.p. 194°–196° C.

IR (Nujol): 1788, 1624, 1546 cm$^{-1}$ $^1$H NMR: 12.66 (br.s., 1H), 8.02 (d, 1H, J=5.9 Hz), 2.29 (d, 1H, J=2.2 Hz)

Analysis: Calcd. for C$_8$H$_5$O$_4$N$_2$F: C, 45.29; H, 2.38; N, 13.21.

Found: C, 45.39; 1H, 2.41; N, 13.31.

EXAMPLES 2–6

Employing the procedure of Example 1 and starting with appropriate 2-benzoxazolones, the following 6-nitro-2-benzoxazolones were prepared.

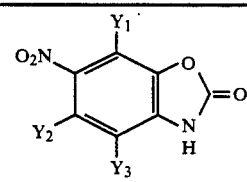

| Example No. | Y$_1$ | Y$_2$ | Y$_3$ | m.p. | IR (cm$^{-1}$) | NMR |
|---|---|---|---|---|---|---|
| 2 | CH$_3$ | F | H | 214–216 | 3250, 1750, 1630, 1540, 1480 | 12.39 (br.s., 1H), 7.24 (d, 1H, J=9.5 Hz), 2.36 (s, 3H) |
| 3 | F | F | H | | | 9.83 (br.s., 1H), 6.94 (dd, 1H, J=10, 2 Hz) |
| 4 | H | CH$_3$ | F | 182–184 | 3280, 1800, 1764, 1660, 1540 | 12.89 (br.s., 1H), 7.98 (s, 1H), 2.44 (d, 3H, J=2.2 Hz) |
| 5 | H | CH$_3$O | F | 156–158 | 1760, 1660, 1550 | 12.95 (s, 1H), 7.91 (d, 2H, J=1.6 Hz), 3.97 (s, 3H) |
| 6 | CH$_3$ | CH$_3$ | H | | | |

EXAMPLE 7

6-Amino-5-fluoro-4-methyl-2-benzoxazolone

A mixture of 1.80 g (8.50 mmoles) of 5-fluoro-4-methyl-6-nitro-2-benzoxazolone (Example 1) and 180 mg of 5% Pd/c in ethanol was shaken in a Parr shaker under one atmosphere of hydrogen gas at room temperature for 8 hours. The reaction mixture was filtered through celite and the filtrate evaporated to solids. Crude product was recrystallized from methanol to yield 1.04 g of the title compound as pale brown solids: m.p. 209°–212° C. (dec).

IR (KBr): 3230, 1804, 1776, 1742 cm$^{-1}$ $^1$H NMR: 11.32 (br.s., 1H), 6.55 (d, 1H, J=6.6 Hz), 4.84 (d, 2H, J=5.9 Hz), 2.16 (d, 3H, J=1.5 Hz)

Analysis: Calcd. for $C_8H_7O_2N_2F$: c, 52.75; H, 3.87; N, 15.38.

Found: C, 53.05; H, 4.13; N, 15.27.

EXAMPLES 8–12

Employing the procedure of Example 7 and starting with appropriate 6-nitro-2-benzoxazolones in place of 5-fluoro-4-methyl-6-nitro-2-benzoxazolone, the following variously substituted 6-amino-2-benzoxazolones were prepared.

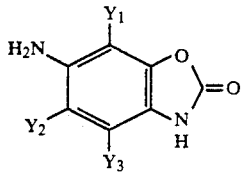

| Example No. | $Y_1$ | $Y_2$ | $Y_3$ | m.p. (°C.) | IR (cm$^{-1}$) | NMR |
|---|---|---|---|---|---|---|
| 8 | CH$_3$ | F | H | 215–216 | 3210, 1790, 1770, 1746, 1662, 1480 | 11.12 (br.s., 1H), 6.72 (d, 1H, J=9.5 Hz), 4.67 (d, 2H, J=5.9 Hz), 2.11 (S, 3H) |
| 9 | F | F | H |  | 3150, 1850, 1815, 1750 | 11.56 (br.s., 1H), 6.80 (dd, 1H, J=10.2 Hz), 5.00 (S, 2H) |
| 10 | H | CH$_3$ | F | 179–182 (dec) | 3450, 3170, 1780, 1670, 1634 |  |
| 11 | H | CH$_3$O | F | 180–183 | 3470, 3360, 3200, 3120, 1884, 1854, 1740, 1660 | 11.66 (br.s., 1H), 6.46 (d, 1H, J=1.5 Hz), 5.04 (S, 2H), 3.72 (S, 3H) |
| 12 | CH$_3$ | CH$_3$ | H | 212 (dec) | 3470, 3390, 3200, 1770, 1650, 1630 | 10.94 (br.s., 1H), 6.56 (S, 1H), 4.42 (br.s., 2H), 2.08 (S, 3H), 2.07 (S, 3H) |

EXAMPLE 13

6-Benzylamino-5-fluoro-4-methyl-2-benzoxazolone

A mixture of 6-amino-5-fluoro-4-methyl-2-benzoxazolone (Example 7 0.43 g, 2.40 mmoles) and benzaldehyde (0.26 g, 2.40 mmoles) in ethanol (2 ml) was refluxed for 2.5 hours. After cooling, the precipitated product was collected and washed with cold ethanol. To a mixture of the precipitate (0.63 g) and ethanol (8 ml) was added portionwise sodium borohydride (300 mg) at room temperature under stirring. Stirring continued for 15 hours. The reaction mixture was diluted with ethyl acetate and washed with water. The aqueous phase was extracted twice with ethyl acetate. The combined ethyl acetate extracts were dried over sodium sulfate and evaporated to dryness. The residue was purified by column chromatography on silica gel, eluting with ethyl acetate/hexane (1:4 by volume) to give the title compound (0.56 g). Recrystallization from methanol gave 0.44 g (68%) of the title compound as pale orange needles: m.p. 204°–206° C.

IR (KBr): 3440, 3170, 3100, 3040, 1756, 1656, 1508 cm$^{-1}$

1H NMR: 11.30 (br.s., 1H), 7.29 (m, 5H), 7.23 (d, 1H, J=1.5 Hz), 6.41 (t, 1H, J=6.6 Hz), 4.30 (d, 2H, J=5.1 Hz), 2.13 (d, 3H, J=1.5 Hz).

Analysis: Calcd. for $C_{15}H_{13}O_2N_2F$: C, 66.17; H, 4.81; N, 10.29

Found: C, 66.08; H, 4.86; N, 10.23

EXAMPLES 14–18

Employing the procedure of Example 13 and starting with appropriate 6-amino-2-benzoxazolones in place of 6-amino-5-fluoro-4-methyl-2-benzoxazolone, the following variously substituted 6-benzylamino-2-benzoxazolones were prepared.

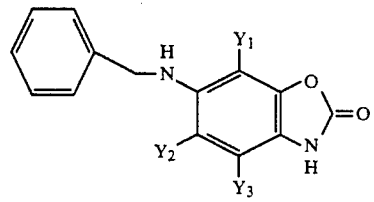

| Example No. | $Y_1$ | $Y_2$ | $Y_3$ | m.p. (°C.) | IR (cm$^{-1}$) | NMR |
|---|---|---|---|---|---|---|
| 14 | CH$_3$ | F | H | 144 | 3230, 1730, 1635, 1450 | 11.31 (br.s., 1H), 7.30 (m, 5H), 6.70 (d, 1H, J=11.0 Hz), 4.89 (t, 1H, J=6.80 Hz) |
| 15 | F | F | H | 175–176 | 3620, 3300, 1800, 1763 | 11.64 (br.s, 1H), 7.29–7.17 (m, 5H), 6.78 (dd, 1H, J=10, 2 Hz), 5.61–5.50 (m, 1H), 4.31 (d, 2H, J=6 Hz) |
| 16 | H | CH$_3$ | F | 184–185 | 3480, 3190, 3120, 1765, 1628 | 11.56 (br.s., 1H), 7.37–7.17 (m, 5H), 6.22 (S, 1H), 5.85 (t, 1H, J=5.9 Hz), 4.34 (d, 2H, J=4.0 Hz), 2.1 (d, 3H, J=2.2 Hz) |
| 17 | H | CH$_3$O | F |  |  |  |
| 18 | CH$_3$ | CH$_3$ | H | 194–196 | 3150, 2650, 2600, 2550, 2470, 1780, 1620 | 11.88 (br.s), 7.39–7.32 (m, 5H), 6.85 (S, 1H), 4.43 (S, 1H), 4.43 (S, 2H), 3.70 (br.s., 1H) |

EXAMPLE 19

4-Fluoro-5-methoxy-6-(3-methylbenzylamino)-2-benzoxazolone

Following the procedure of Example 13, 6-amino-4-fluoro-5-methoxy-2-benzoxazolone (Example 11) was reacted with 3-tolualdehyde and the resulting product was reduced with sodium borohydride to give the title compound: m.p. 160°–161° C.

IR (Nujol): 3240, 1768, 1634, 1520 cm$^{-1}$.

1H NMR: 11.68 (br.s., 1H), 7.21–7.11 (m, 3H), 7.02 (d, 1H, J=6.6 Hz), 6.30 (d, 1H, J=1.5 Hz), 6.02 (t, 1H, J=6.6 Hz), 4.28 (d, 2H, J=5.9 Hz), 3.78 (S, 3H), 2.27 (S, 3H).

EXAMPLES 20-22

In like manner employing appropriate aldehydes and 6-amino-4-fluoro-5-methyl-2-benzoxazolone in the procedure of Example 13 afforded the following compounds.

| Example No. | R | m.p. (°C.) | IR (cm$^{-1}$) | NMR |
|---|---|---|---|---|
| 20 | (3-methylbenzyl) Free base | 192–193 | 3440, 1766, 1666, 1632, 1608 | 11.55 (br.s., 1H), 7.21–7.11 (m, 3H), 7.02 (d, 1H, J=6.6 Hz), 6.21 (S, 1H), 5.81 (t, 1H, J=6.2 Hz), 4.29 (d, 2H, J=4.5 Hz), 2.28 (S, 3H), 2.07 (d, 3H, J=2.2 Hz) |
| 21 | Hydrochlorate | 183–199 (dec) | 2730, 1814, 1796, 1662, 1634, 1588 | 11.67 (br.s., 1H), 7.22–7.13 (m, 3H), 7.04 (d, 1H, J=7.3 Hz), 6.31 (S, 1H), 4.30 (S, 2H), 2.27 (S, 3H), 2.09 (d, 3H, J=2.2 Hz) |
| 22 | (pyridin-3-yl) | 232–233 | 3460, 1810, 1770, 1668, 1638, 1602, 1584, 1520 | 11.60 (br.s., 1H), 8.58 (d, 1H, J=1.5 Hz), 8.42 (dd, 1H, J=1.5, 4.9 Hz), 7.74 (ddd, 1H, J=1.5, 1.5, 7.8 Hz), 7.33 (dd, 1H, J=4.9, 7.8 Hz), 6.31 (S, 1H), 5.88 (t, 1H, 5.9 Hz), 4.37 (d, 2H, J=5.9 Hz), 2.07 (d, 3H, J=2.2 Hz) |

EXAMPLE 23

4-Fluoro-5-methyl-[6-[3-(pyridin-3-yl)propyl]amino]-2-benzoxazolone 3-(pyridin-3-yl)propyl aldehyde (15.2 g, 113 mmol) was added to a solution of 6-amino-4-fluoro-5-methyl-2-benzoxazolone (17.4 g, 96 mmol) in MeOH (600 ml). The mixture was stirred for 1 hour at room temperature. AcOH (1 ml) was added, followed by an addition of sodium cyanoborohydride (8.17 g, 130 mmol). Stirring was continued for 5 hours. The reaction mixture was concentrated in vacuo, and the residue was treated with water. The resulting precipitate was collected and washed with water. This crude product was recrystallized, to give the titled compound m.p.: 280° C. (dec.).

E.A.: Calcd.: C 63.77%, H 5.35%, N 13.95%,
Found: C 63.94% H 5.46% N 14.01%
IR(Nujol): 3450, 1760, 1660 cm$^{-1}$
1H NMR: 8.46 (1H, d, J=2 Hz), 8.38 (1H, dd, J=5.2 Hz), 7.58–7.62 (1H, m) 7.40 (1H, dd, T=5.5 Hz), 6.45 (1H, S), 3.05–3.01 (2H, m) 2.59–2.66 (2H, m), 2.01 (3H, S), 1.83–1.91 (2H, m).

EXAMPLE 24

1. 3-Formyl-tetrahydro-2H-pyran

5% Pd/C (5 g) was added to a solution of 3-formyl-5,6-dihydro-2H-pyran[1] (95.8 g, 0.81 mol) in MeOH (200 ml) at room temperature, and the mixture was stirred for 15 hours under a hydrogen atmosphere. The catalyst was filtered off, and the solvent was removed in vacuo. The resulting oil was distilled under reduced pressure (84°–85° C./36–39 mmHg) to give 3-formyl-tetrahydro-2H-pyran (79.4 g, 85% yield).
[1] Japan Kokaitokkyo Koho 84167584 (1984)

1H NMR: (CDCl$_3$), 1.59–1.72 (m, 2H), 1.82–1.98 (m, 2H), 2.44–2.54 (m, 1H), 3.52–3.61 (m, 1H), 3.68–3.74 (m, 1H), 3.82 (dd, 1H, J=11.7, 6.6 Hz), 3.97 (dd, 1H, J=11.7, 3.7 Hz), 9.72 (s, 1H).

2. 4-Fluoro-5-methyl-6-(tetrahydro-2H-pyranyl)methylamino-2-benzoxazolone

3-Formyltetrahydro-2H-pyran (12.9 g, 113 mmol) was added to a solution of 6-amino-4-fluoro-5-methyl-2-benzoxazolone (17.4 g, 96 mmol) in MeOH (600 ml). The mixture was stirred for 1 hour at room temperature. AcOH (1 ml) was added, followed by an addition of sodium cyanoborohydride (8.17 g, 130 mmol). Stirring was continued for 5 hours. The reaction mixture was concentrated in vacuo, and the residue was treated with water. This crude product was recrystallized from EtOH, to give the titled compound.

1H NMR: (270 MHz, CDCl$_3$-TMS), 11.58 (1H, s), 6.40 (1H, s), 4.99–5.03 (1H, m), 3.83 (1H, br.d, J=9 Hz), 3.72 (1H, br.d, J=11 Hz), 3.09–3.20 (1H, m), 2.86–2.95 (2H, m), 2.00 (3H, s), 1.82–1.86 (1H, m), 1.43–1.61 (4H, m) 1.14–1.25 (1H, m)
IR (Nujol): 3430, 2700, 1780, 1670, 1635 cm$^{-1}$
E.A.: Calcd. for $C_{14}H_{17}O_3N_2F$: C 59.99%, H 6.11%, N 10%,
Found: C 59.65%, H 6.37%, N 9.91%
mp: 165.8°–166.2° C.

Preparation A

5-Fluoro-4-methyl-2-benzoxazolone

A.1 4-Fluoro-2-nitroanisole

Sodium hydride 4.59 g (7.64 g as 60% mineral oil dispersion) was suspended in DMF (64 ml) under a nitrogen atmosphere. To this was added 4-fluoro-2-nitrophenol in 64 ml DMF over 30 minutes at room temperature. Stirring continued for 15 minutes. Methyl iode was then added over 15 minutes. The mixture was further stirred for 3 hours. The precipitates which formed were filtered off and the filtrate was evaporated to dryness. The residue was dissolved in benzene and the filtrate washed with water, aqueous sodium hydroxide and with brine. This solution was dried over sodium sulfate and evaporated to give 21.1 g of the title compound: m.p. 60° C.

IR(KBr): 1527, 1270cm$^{-1}$
NMR(CDCl$_3$): 7.61 (dd, 1H, J=2.9, 8.1 Hz), 7.29 (ddd, 1H, J=2.9, 7.3, 8.8 Hz), 7.07 (dd, 1H, J=4.0, 8.8 Hz), 3.95 (S, 3H)

A.2 2-Amino-4-fluoroanisole

A solution of 20.5 g of 4-fluoro-2-nitroanisole in ethyl acetate was hydrogenated over 5% palladium carbon (2 g) at room temperature for 16 hours. The catalyst was removed by filtration and the filtrate evaporated to leave 17 g of the title compound as a brown oil.

IR(neat): 3500, 3400, 1624, 1516, 1222cm$^{-1}$
NMR(CDCl$_3$): 6.66 (dd, 1H, J=4.8, 8.8 Hz), 6.43 (dd, 1H, J=2.9, 9.5 Hz), 6.37 (ddd, 1H, J=2.9, 8.8, 8.8 Hz), 3.88 (br.s., 2H), 3.81 (S, 3H).

A.3 2-(N-tert-butoxycarbonylamino)-4-fluoroanisole

A solution of 2-amino-4-fluoroanisole (17 g, 120 mmoles) in 120 ml tetrahydrofuran was combined with di-tert-butyl dicarbonate (29 g, 132 mmoles). The mixture was refluxed for 50 hours. Upon cooling the solvent was removed and the residue was dissolved in benzene. The benzene solution was washed with 1M citric acid solution and with brine, dried over sodium sulfate, and evaporated to leave a residual oil. This oil was distilled to give 23.3 g of 2-(N-tert-butoxycarbonylamino)-4-fluoroanisole as a colorless oil: bp 112°-114° C./0.2 mmHg.

A.4 2-(N-tert-Butoxycarbonylamino)-4-fluoro-3-methylanisole

To a stirred solution of 22.6 g (100 mmoles) of the preceding compound in 400 ml tetrahydrofuran, at −78° C., was added dropwise a 1.4M solution of sec-butyl lithium (171 ml, 240 mmoles) under nitrogen over 40 minutes. After stirring for 30 minutes at −78° C., a solution of methyl iodide (14.1 g, 100 mmoles) in 150 ml tetrahydrofuran was added over 20 minutes. After maintaining the reaction mixture at −78° C., it was allowed to warm up to room temperature. Stirring continued for 1.5 hours. Water (5 ml) was added to quench the reaction. The reaction mixture was diluted with benzene, washed with water and with brine, and dried over sodium sulfate. Removal of the Solvent gave a viscous oil, which was purified by vacuum distillation to yield 13.3 g of the title compound as a solid; m.p. 81°-82° C.

IR(Nujol): 3320, 1740, 1692, 1250cm$^{-1}$

NMR(CDCl$_3$): 6.86 (dd, 1H, J=8.8, 8.8 Hz), 6.64 (dd, 1H, J=4.8, 9.2 Hz), 6.12 (br.s., 1H), 3.80 (S, 3H), 2.18 (d, 3H, J=2.2 Hz), 1.50 (S, 9H).

A.5 2-Amino-4-fluoro-3-methylphenol

To a mixture of mercaptoethane (56 ml) and dichloromethane (56 ml) was added aluminum chloride (22.4 g, 168 mmoles) under stirring at 0° C. To this was then added 2-(N-tert-butoxycarbonylamino)-4-fluoro-3-methylanisole (12.6 g, 56 mmoles) slowly at room temperature. Stirring continued for 1½ hours. The reaction was quenched by adding ice and water and the solution acidified with 1N HCl. The organic substance was extracted with ethyl acetate (x3). The combined extracts were washed with NaHCO$_3$ and with brine, dried over sodium sulfate and concentrated to give a solid. Recrystallization from chloroform gave 3.15 of pure title product; m.p. 118°-121° (dec).

IR(KBr): 3410, 3330, 3250, 2950, 1590, 1490, 1244cm$^{-1}$

NMR: 8.94 (br.s., 1H), 6.46 (dd, 1H, J=5.1, 8.8 Hz), 6.17 (dd, 1H, J=8.8, 8.8 Hz), 4.51 (br.s., 2H), 1.96 (d, 3H, J=2.2 Hz).

To a solution of 2-amino-4-fluoro-3-methylphenol (3.00 g, 21 mmoles) in tetrahedron (100 ml) was added dropwise trichloromethyl chloroformate (TCF, 5 ml, 42 mmoles) at 5° C. under stirring. Stirring continued for 40 minutes. Water was added to destroy excess TCF. The reaction mixture was diluted with water and extracted twice with ethyl acetate. The combined ethyl acetate extracts were washed with water, aqueous saturated sodium bicarbonate solution, and brine, and dried over magnesium sulfate. Removal of the solvent under reduced pressure gave a crude product, which is recrystallized from ethyl acetate to afford 2.19 g (62%) of the title product as a pale orange solid: m.p. 189°-190° C.

IR (KBr): 3180, 3130, 1780, 1746, 1460, 1222 cm$^{-1}$

1H NMR: 11.89 (br.s., 1H), 7.12 (dd, 1H, J=4.4, 8.8 Hz), 6.87 (dd, 1H, J=8.8, 11.0 Hz), 2.21 (d, 3H, J=1.5 Hz).

Analysis: Calcd. for C$_8$H$_6$O$_2$NF: C, 57.49; H, 3.62; N, 8.38;

Found: C, 57.56; H, 3.55; N, 8.51

Preparation B

5-Fluoro-7-methyl-2-benzoxazolone

B.1 4-Fluoro-6-methyl-2-phenylazophenol

To a mixture of aniline (4.65 g, 50 mmoles), concentrated hydrochloric acid (10 ml, 120 mmoles) and water (25 ml) was added a solution of sodium nitrite (3.5 g, 50 mmoles) in water (13 ml) at 5° C. over a period of 20 minutes. 4-Fluoro-2-methylphenol (6.3 g, 50 mmoles) was dissolved in aqueous sodium hydroxide (6 g of sodium hydroxide dissolved in 50 ml of water), and cooled with ice/water. The freshly prepared benzenediazonium solution was added slowly to the above phenol solution over 20 minutes under stirring. Stirring continued for 1 hour. The resulting orange solid was collected and washed with water. Recrystallization from methanol-water gave an orange needle (5.54 g): m.p. 101°-102° C.

IR(KBr): 3080, 2980, 2930, 1480, 1460, 1280, 1264 cm$^{-1}$

1H NMR(CDCl$_3$): 12.91 (S, 1H), 7.87 (m, 2H), 7.51 (m, 4H), 7.01 (dd, 1H, J=3.3, 8.4 Hz), 2.32 (S, 3H).

B.2 2-Amino-4-fluoro-6-methylphenol

A mixture of 5.75 g (25 mmoles) of 4-fluoro-6-methyl-2-phenylazophenol (B1) and 1.1 g of 5% Pd/c in ethyl acetate was shaken in a Parr shaker under hydrogen at room temperature for 17.5 hours. The reaction mixture was filtered through celite and the filtrate concentrated to an oil which was purified on silica gel eluting with hexane-ethyl acetate, giving 3.2 g of a white solid: m.p. 97° C. (dec).

IR(KBr): 3400, 2950, 1620, 1500, 1196 cm$^{-1}$

1H NMR(CDCl$_3$): 7.40 (br.s., 1H), 6.34 (dd, 2H, J=2.9, 14.7 Hz), 6.31 (dd, 2H, J=2.9, 13.9 Hz), 3.8 (br.s., 2H), 2.20 (S, 3H).

Following the procedure of Preparation A, the product (3.1 g) of B2 was cyclized to give 2.12 g of the title compound: m.p. 210° C. (dec).

IR(KBr): 3310, 2950, 2800, 1780, 1550, 1500cm$^{-1}$

1H NMR: 11.73 (br.s., 1H), 6.82 (m, 2H), 2.29 (S, 3H).

Preparation C

5,7-Difluoro-2-benzoxazolone

C.1 2,4-Difluoro-6-nitrophenol

To a mixture of nitric acid (100 ml) and acetic acid (100 ml) was added a solution of 2,4-difluorophenol (13 g, 100 mmoles) in acetic acid (100 ml) dropwise at −5° under stirring. Stirring continued for 2 hours. The reaction mixture was poured into ice. The precipitate was collected, washed with water and dried to leave 11.26 g of a yellow solid. The material was used in the next step without further purification.

1H NMR: 11.15 (br.s., 1H), 7.68-7.79 (m, 2H).

C.2 6-Amino-2,4-difluorophenol

The product from Cl (2.5 g, 14 mmoles) was hydrogenated over 5% Pd/c in ethanol at room temperature.

The reaction mixture was filtered through celite and the filtrate concentrated to give a brown solid. The material was used in the next step without further purification.

1H NMR: 8.79 (br.s., 1H), 6.18–6.28 (m, 2H), 5.21 (br.s, 2H).

Following the procedure of Preparation A, the product (3.59 g) of C2 was cyclized to give 5.62 g of the title compound as a brown powder.

1H NMR: 12.48 (br.s., 1H), 7.40 (dd, 1H), 7.22–7.26 (m, 1H).

Preparation D

4-Fluoro-5-methyl-2-benzoxazolone

D.1 6-Fluoro-5-methylsalicyclic acid

To a stirred solution of 3-fluoro-4-methyl-1-(methoxymethoxy)-benzene (7.65 g, 45 mmoles) was added 1.6M n-Buli in hexane (34 ml, 54 mmoles) dropwise below −65° C. over 40 minutes. After stirring at −78° C. for 1.5 hours the cooling bath was removed and carbon dioxide gas was bubbled into the solution for 1 hour. Methanol (50 ml) and concentrated hydrochloric acid (30 ml) were added and the reaction mixture was stirred overnight. It was then poured into water and the organic substance extracted with dichloromethane (X2). The combined extracts were washed with water, and extracted with sodium bicarbonate (X3). The aqueous extracts were acidified with concentrated hydrochloric acid and the organic substance extracted with ethyl acetate. The combined extracts were washed with brine, dried over sodium sulfate and evaporated to dryness to give white solids (6.71 g, 39.4 mmoles): m.p. 145°–150° C.

IR(KBr): 3080, 1660, 1622, 1592, 1480cm$^{-1}$

1H NMR: 7.25 (dd, 1H, J=7.3, 8.8 Hz), 6.66 (d, 1H, J=7.3 Hz), 2.12 (d, 3H, J=2.2 Hz).

A mixture of 6-fluoro-5-methylsalicylic acid (6.46 g, 38 mmoles), diphenylphosphoryl azide (10.5 g, 38 mmoles) and triethylamine (3.85 g, 38 mmoles) in toluene was stirred at 100° C. for 42 hours. The reaction mixture was diluted with ethyl acetate and washed with in hydrochloric acid, aqueous saturated sodium bicarbonate solution, and brine. The organic layer was separated, dried over sodium sulfate and concentrated in vacuo. Recrystallization of the residual product from toluene gave 2.71 g (43%) of the title compound, m.p. 149°–150° C.

IR(KBr): 3200, 3100, 1770, 1660, 1634 cm$^{-1}$

1H NMR: 12.89 (br.s, 1H), 7.98 (S, 1H), 2.44 (d, 3H, 2.2 Hz).

Preparation E

4-Fluoro-5-methoxy-2-benzoxazolone

E.1 6-Fluoro-5-methoxysalicyclic acid

According to the procedure for preparation of the product of D1, 3-fluoro-4-methoxy-1-(methoxymethoxy)-benzene gave the title product: m.p. 154°–155° C.

IR (Nujol): 3150, 1872, 1698, 1620, 1600 cm$^{-1}$.

1H NMR(CDCl$_3$): 6.88 (dd, 1H, J=8.8, 9.5 Hz), 6.85 (dd, 1H, J=2.9 12.5 Hz), 6.75 (ddd, 1H, J=1.5, 2.9, 8.8 Hz), 5.10 (S, 2H), 3.85 (S, 3H), 3.47 (S, 3H), Following the procedure of Preparation D, the product of E1 (7.45 g) was cyclized to give 7.68 g of the title product. Recrystallization from toluene afforded a white solid: m.p. 186°–188° C.

IR (Nujol): 1768, 1666, 1634, 1530cm$^{-1}$

1H NMR: 12.19 (br.s., 1H), 7.07 (d, 2H, J=8.8 Hz), 6.84 (dd, 1H, J=8.8, 8.8 Hz), 3.82 (S, 3H).

Preparation F 5, 7-Dimethyl-2-benzoxazolone

A mixture of 2-amino-4, 6-dimethylphenol (6.86 g, 50 mmoles) and urea (6.01 g, 100 mmoles) was heated at 170° C. for 1 hour. After cooling the resulting solid was dissolved in hot ethanol and recrystallized to give 6.05 g of the title compound.

I claim:

1. A compound of the formula:

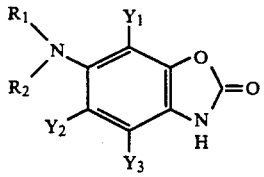

or a pharmaceutically acceptable acid addition salt thereof wherein $R_1$ is hydrogen or $C_1$-$C_3$alkyl; $R_2$ is a group of the formula —(CH$_2$)$_m$—Ar or —(CH$_2$)$_m$—Het wherein m is an integer of 1 to 6 and Ar is phenyl optionally substituted by one or more radicals selected from ($C_1$-$C_3$)alkyl, ($C_1$-$C_3$)alkoxy, ($C_1$-$C_3$)alkylthio, halo, ($C_1$-$C_2$)alkylamino or hydroxyl;

Het is selected from furyl, thienyl, pyridyl, pyrrolyl, imidazolyl, pyranyl, oxazolyl or indazolyl; and $Y_1$, $Y_2$ and $Y_3$ are each independently hydrogen, ($C_1$-$C_3$)alkyl, halo or ($C_1$-$C_3$)alkoxy or trifluoromethyl;

with the proviso that one and only one of $Y_1$, $Y_2$ or $Y_3$ is hydrogen.

2. A compound according to claim 1 wherein m is 1.

3. A compound according to claim 2 wherein $Y_1$ is hydrogen.

4. A compound according to claim 3 wherein $Y_2$ and $Y_3$ are each methyl or fluoro.

5. A compound according to claim 2 wherein $Y_3$ is hydrogen.

6. A compound according to claim 5 wherein $Y_1$ and $Y_2$ are each methyl or fluoro.

7. A compound according to claim 1, said compound being
6-benzylamino-4-fluoro-5-methyl-2-benzoxazolone.

8. A compound according to claim 1, said compound being
6-benzylamino-5-fluoro-4-methyl-2-benzoxazolone.

9. A pharmaceutical composition for the treatment of an allergic or inflammatory condition in a mammal which comprises a compound of claim 1 in a pharmaceutically-acceptable carrier or diluent.

10. A method of treating an allergic or inflammatory condition which comprises administering to a mammal suffering from an allergic or inflammatory condition an antiallergic or antiinflammatory effective amount of a compound of claim 1.

* * * * *